(12) United States Patent
Redano

(10) Patent No.: US 6,428,478 B2
(45) Date of Patent: Aug. 6, 2002

(54) METHOD FOR ACCELERATING THE DELIVERY OF A VASODILATING AGENT TO THE PENIS

(76) Inventor: Richard T. Redano, 2605 Werlein St., Houston, TX (US) 77005

( * ) Notice: Subject to any disclaimer, the term of this patent is extended or adjusted under 35 U.S.C. 154(b) by 0 days.

(21) Appl. No.: 09/732,274

(22) Filed: Dec. 7, 2000

Related U.S. Application Data

(60) Division of application No. 09/315,867, filed on May 20, 1999, now Pat. No. 6,221,021, which is a continuation-in-part of application No. 08/926,209, filed on Sep. 9, 1997, now Pat. No. 5,947,901.

(51) Int. Cl.7 .................................................. A61B 8/00
(52) U.S. Cl. ........................ 600/439; 600/454; 600/504; 600/38; 601/2; 601/46; 604/517
(58) Field of Search ............................... 601/2, 71, 46; 600/439, 454, 504, 38; 604/22, 500, 501, 507, 514, 516, 517

(56) References Cited

U.S. PATENT DOCUMENTS

| 4,252,786 A | | 2/1981 | Weiss et al. | |
| 4,666,702 A | | 5/1987 | Junginger | |
| 4,887,594 A | * | 12/1989 | Siegel | 601/46 |
| 5,270,323 A | | 12/1993 | Milne, Jr. et al. | |
| 5,286,488 A | | 2/1994 | Manikas et al. | |
| 5,482,039 A | * | 1/1996 | Place | 604/517 |
| 5,549,544 A | * | 8/1996 | Young et al. | 601/2 |
| 5,565,466 A | | 10/1996 | Gioco | |
| 5,690,608 A | * | 11/1997 | Watanabe et al. | 601/2 |
| 5,731,339 A | | 3/1998 | Lowrey | |
| 5,820,587 A | * | 10/1998 | Place | 604/500 |
| 5,823,991 A | * | 10/1998 | Shim | 604/500 |
| 6,083,214 A | * | 7/2000 | Ross et al. | 604/500 |
| 6,251,076 B1 | * | 6/2001 | Hovland et al. | 600/454 |

* cited by examiner

Primary Examiner—Ruth S. Smith

(57) ABSTRACT

The present invention is directed toward a method for accelerating the delivery of a vasodilating agent to the penis. The method of the present invention comprises ingesting a vasodilating agent into the body at a point of ingestion external to the penis, and transmitting ultrasound energy into the penis at a sufficient frequency and intensity to increase hemodynamic activity.

19 Claims, 3 Drawing Sheets

METHOD FOR ACCELERATING THE DELIVERY OF A VASODILATING AGENT TO THE PENIS

CROSS REFERENCE TO RELATED APPLICATIONS

This is a divisional of patent application Ser. No. 09/315,867 filed on May 20, 1999, now U.S. Pat. No. 6,221,021, which is a continuation-in-part application of application Ser. No. 08/926,209, filed on Sep. 9, 1997, and which issued as U.S. Pat. No. 5,947,901.

BACKGROUND OF THE INVENTION

1. Field of the Invention

The present invention is directed toward a method for accelerating the delivery of a vasodilating agent to the penis. The method of the present invention comprises ingesting a vasodilating agent into the body at a point of ingestion external to the penis, and transmitting ultrasound energy into the penis at a sufficient frequency and intensity to increase hemodynamic activity.

2. Description of the Prior Art

Erectile dysfunctionality may result from neurogenic, vasculogenic, hormonal, and/or psychogenic causes. The term "erectile dysfunctionality", as used herein, refers to the inability or impaired ability of a male patient to experience a penile erection. The urological arts have devised a number of therapies for treating erectile dysfunctionality. These therapies include psychological, pharmacological, and electrical therapies.

A method and device for electrically stimulating a penile erection is disclosed in U.S. Pat. No. 4,585,005 to Lue et al. The method disclosed in Lue includes the implantation of an electrode on the cavernous nerves The electrodes of Lue are connected to a receiver that is subcutaneously implanted in the patient. The method and device disclosed in Lue requires surgery. Additionally, if the device disclosed in Lue malfunctions, surgery is required to remove it. Surgery is expensive and time consuming. Additionally, many patients may have emotional or psychological aversions to having electrodes implanted in their penis.

An apparatus for electrically stimulating penile tissue to cause a penile erection is disclosed in U.S. Pat. No. 5,571,118 to Boutos. Boutos discloses the use of a ring having a conductive surface that is placed on the penis and/or the scrotum. There is a risk that such a device may short circuit, if used in an electrically conductive environment, such as a hot tub. This is a major drawback of external electrical therapies, as contrasted with external ultrasound therapies. The use of ultrasound transducers on submerged patients has been applied in other nonanalogous arts, such as extracorporeal shock wave lithotripsy.

An apparatus for electrically stimulating a penile erection is disclosed in U.S. Pat. Nos. 4,542,753 and 4,663,102 to Brennan et al. Brennan discloses a body member for insertion into the rectum of a patient. The body member comprises surface mounted electrodes. Brennan teaches insertion of the body member sufficiently deep into the patient for at least one electrode to contact the prostate gland. The device disclosed by Brennan is highly invasive. Patients may experience physical discomfort from the rectal insertion of the device disclosed in Brennan.

Pharmacological therapies for erectile dysfunctionality include the injection of drugs into the penis. Such methods are disclosed in U.S. Pat. No. 5,236,904 to Gerstengerg et al. and U.S. Pat. No. 4,127,118 to Latorre. Many male patients find the thought of jabbing a hypodermic needle into their penis to be discomforting. Penile injections may also result in the buildup of scar tissue, bleeding, and persistent prolonged erection (priapism). The unacceptability of therapies requiring the intracavernosal injection of drugs into the penis is well documented in the urological arts (See U.S. Pat. No. 5,482,039 to Place et al. and U.S. Pat. No. 5,731,339 to Lowrey; and Padma-Nathan, *Treatment of Men With Erectile Dysfunction With Transurethral Alprostadil,* The New England Journal of Medicine, 336:1–7, Jan. 2, 1997).

Other pharmacological therapies for erectile dysfunctionality include delivering a drug directly into the urethra of a patient. Methods and devices for transurethral delivery of drugs into the penis are disclosed in U.S. Pat. Nos. 5,242,391 and 5,482,039 to Place et al. These transurethral drug delivery methods involve inserting a shaft into the urethra. The insertion of a shaft up the urethra may cause discomfort in many patients or be objectionable for many of the same reasons that penile hypodermic needle injections are objectionable.

Pharmacological agents for the treatment of erectile dysfunctionality, including vasodilators such as phosphodiesterase (PDE) inhibitors, or alpha adrenergic blockers, may also be delivered orally, transmucosally, transdermally, intranasally and/or rectally. Oral medications are available, pursuant to U.S. Food & Drug Administration (FDA) regulations, under the trademarks VIAGRA (a PDE inhibitor) from Pfizer, Inc. of New York, N.Y., and VASOMAX (an alpha adrenergic blocker) from Zonagen, Inc. of The Woodlands, Texas, or its licensees. Such oral medications are described in U.S. Pat. No. 5,731,339 to Lowrey and U.S. Pat. No. 5,565,466 to Gioco, et al.

Orally, transmucosally, transdermally, intranasally, and/or rectally ingested pharmacological agents for the treatment of erectile dysfunctionality must be dissolved into the blood stream and transported through the body to the penis. Methods of transporting such pharmacological agents to a desired site of effect, are disclosed in U.S. Pat. No. 5,565,466 and are incorporated herein, in their entirety. The time required for such pharmacological agents to be dissolved into the blood stream and transported to a site where they will relax the smooth muscle tissue in the corpora cavernosa, resulting in increased penile hemodynamic activity sufficient to cause an erection (referred to herein as the "circulatory medication response time"), can be as long as one hour (see website of Zonagen, Inc). This time period can be unsatisfactory to many men and their consorts, who desire spontaneity in their sexual relations.

The present invention provides an ultrasonic therapy for hemodynamic stimulation of the penis that does not require (1) the injection of drugs into the penis, (2) surgical implantation of electrodes into the penis, or (3) the insertion of electrodes into the rectum. The method of the present invention may be used in an electrically conductive medium, such as a pool or hot tub, without the short circuiting risk present in prior art methods of electrotherapy for penile dysfunctionality. The present invention may be used to reduce the circulatory medication response time by accelerating the circulation of blood comprising a vasoactive or vasodilating agent, thereby reducing its transport time.

SUMMARY OF THE INVENTION

Blood is the hydraulic driving fluid that provides the mass increase and force which result in a penile erection. Under normal conditions, a penile erection occurs when the mass flow rate of blood into the penis exceeds the mass flow rate of blood out of the penis for a certain time interval. Vasculogenic erectile dysfunctionality may result from a restriction or blockage of blood flow into the penis or from excess blood flow out of the penis. The present invention is aimed at treating vasculogenic erectile dysfunctionality that results from inadequate blood flow into the penis. The present invention may also be used with devices intended to restrict the venous outflow of blood from the penis, such as the venous flow controller sold under the trademark ACTIS by Vivus, Inc. of Menlo Park, Calif.

The present invention provides a method for stimulating hemodynamic activity within a penis. The first method step of the present invention is coupling an ultrasound source to a penis. Genital lesions, such as warts or herpes simplex Type-2 lesions, can absorb and/or attenuate ultrasound thereby reducing the therapeutic effectiveness of the present invention. Accordingly, in a preferred embodiment, the ultrasound source is coupled to a lesion free region of the outer surface of a penis.

The second method step of the present invention is transmitting ultrasound energy into the corpora cavernosum of the penis at a sufficient frequency and intensity to increase hemodynamic flow within the penis. The frequency used is a function of the depth of desired penetration into the corpora cavernosum.

Initially, a frequency in the range of 2.5–3.5 MHz is desirable. As hemodynamic activity in the penis increases and the penis expands circumferentially, it is desirable to reduce the frequency of ultrasound energy from the initial frequency to a reduced frequency in the range of 1.8–2.5 MHz. The precise values of initial and reduced frequencies will be a function of the diameter of the penis being treated.

A portion of the ultrasound energy transmitted into the body is converted to thermal energy. The increased blood flow resulting from the use of the present invention provides a thermal transport medium for transporting and dispersing thermal energy introduced from the transmission of ultrasound energy. This thermal transport helps to minimize localized temperature increases within the penis. In a preferred embodiment, the ultrasound energy is emitted from one or more ultrasound transducers housed within a portable housing. Localized temperature increases can be further minimized by moving the portable housing relative to the penis being treated so as to disperse the transfer of thermal energy in the corpora cavernosum.

The present invention also provides a method for monitoring the effect of the stimulation therapy of the present invention. The present invention also includes ultrasonographically measuring one or more hemodynamic parameters within the penis. These hemdynamic parameters may include blood flow velocity, blood pressure, and/or blood temperature. The measured hemodynamic parameters can be graphically displayed to provide a real time indication of hemodynamic and/or thermal-hydraulic parameters within the penis. The measured hemodynamic parameters may be transmitted to a remote terminal for analysis by a remotely located health care professional. Alternatively, the measured hemodynamic parameters may be analyzed by an expert system located either remotely or with the patient.

The present invention is also directed toward an apparatus for stimulating hemodynanic activity within a penis. The apparatus of the present invention comprises an ultrasound generator, and a portable housing coupled to the ultrasound generator. The housing comprises at least one ultrasound trigger and a first transducer mounting assembly. The invention further comprises a position adjuster coupled to the first transducer mounting assembly and a second transducer mounting assembly mounted across from the first transducer mounting assembly. The second transducer mounting assembly is coupled to the position adjuster.

A first ultrasound emitter is mounted in the curved lower transducer mounting assembly. The first ultrasound emitter is connected to the ultrasound trigger and to the ultrasound generator. A second ultrasound emitter is mounted in the curved second transducer mounting assembly. The second ultrasound emitter is connected to the ultrasound trigger and to the ultrasound generator. The apparatus of the present invention may also be used to ultrasonographically measure one or more penile hemodynamic parameters.

DESCRIPTION OF THE PREFERRED EMBODIMENTS

Figure 2:
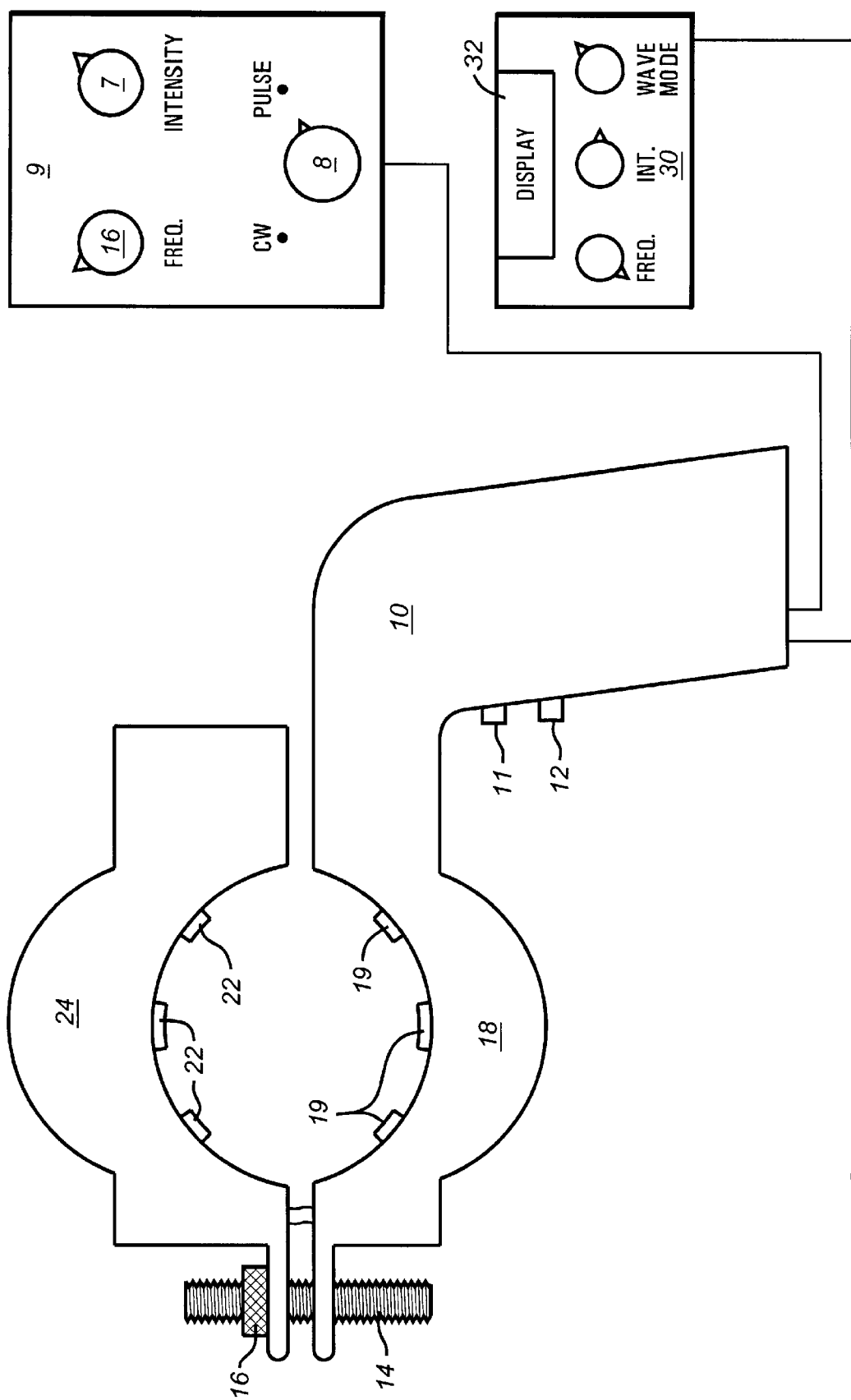
FIG. 2 is a front view of a first apparatus embodiment of the present invention.

The apparatus of the present invention comprises an ultrasound generator 9 and a portable housing 10 coupled to the ultrasound generator, as shown in FIG. 2. The portable housing comprises a first transducer mounting assembly 18. In a preferred embodiment, the lower transducer mounting assembly is curved. An ultrasound trigger 11 is mounted in the housing and electrically coupled to the generator.

In a preferred embodiment, the ultrasound generator is capable of selectively generating pulsed or continuous wave ultrasound energy. This selective generation may be accomplished by a control knob or switch 8, as shown in FIG. 2. In a preferred embodiment, the ultrasound generator fiber comprises frequency controls 6 and intensity controls 7, as shown in FIG. 2. In a preferred embodiment, the ultrasound generator is capable of generating ultrasound energy within a frequency range of 1.8–3.5 MHz and within an intensity range of 1.0–2.0 watts/square centimeter.

Figure 4:
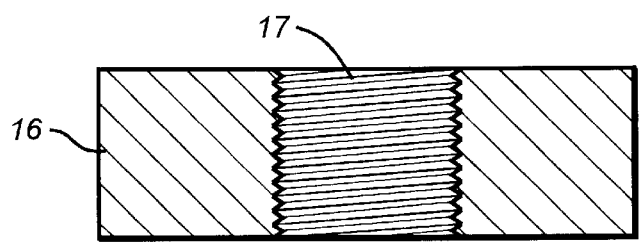
FIG. 4 is a side cross sectional view of the rotatable adjusting wheel of the present invention.

A position adjuster is coupled to the first transducer mounting assembly. In the preferred embodiment shown in FIGS. 2 and 4, the adjuster comprises a threaded rod 14 and a rotatable adjusting wheel 16, comprising a centrally located female threaded channel 17. The channel thereby engages the rod such that when the wheel is rotated, the rod is axially displaced.

It is known in the ultrasound arts that a satisfactory ultrasound coupling is necessary for effective delivery of ultrasound energy to a patient for therapeutic or diagnostic purposes. The position adjuster provides a mechanism for maintaining a satisfactory ultrasound coupling as the penis expands circumferentially as a result of increased hemodynamic activity. As shown in FIG. 2, the position adjuster can be used to control the separation distance between the first and second mounting assemblies. The position adjuster also makes the present invention suitable for use with different patients having varied physical sizes.

The apparatus and method of the present invention may be practiced by the patient, after proper training, without assistance from another person. In the preferred embodiment shown in FIG. 2, the portable housing has a pistol type grip, thereby allowing the user to operate the trigger or triggers with one hand, while manipulating the position adjuster with the other hand, as needed to maintain a suitable ultrasound coupling during penile expansion. The placement of the triggers and axial position adjuster on opposite sides of the housing facilitates the user's ability to easily use both hands to simultaneously manipulate the trigger and the position adjuster.

The invention further comprises an second transducer mounting assembly 24 mounted across from the first transducer mounting assembly. In a preferred embodiment, the second transduced mounting assembly is mounted in alignment with the first transducer mounting assembly. In another preferred embodiment, the second transducer mounting assembly is curved. The second transducer mounting assembly is coupled to the position adjuster. The radii of curvature of the first and second transducer mounting assemblies are sized such that the first and second transducers can be coupled to the outer surface of a penis.

A first ultrasound emitter 19 is mounted in the first transducer mounting assembly. The first transducer is connected to the ultrasound trigger and to the ultrasound generator. Electrical and/or electronic circuitry suitable for connecting ultrasound transmitters to an ultrasound generator are described in the following U.S. Pat. No. 3,735,756 to Richards; U.S. Pat. No. 5,578,060 to Pohl et al.; and U.S. Pat. No. 4,484,569 to Driller et al. The full disclosures of these U.S. Patents is incorporated herein by reference.

A second ultrasound emitter 22 is mounted in the second transducer mounting assembly, as shown in FIG. 2. The second ultrasound emitter is connected to the ultrasound trigger and to the ultrasound generator. In a preferred embodiment, the first and second ultrasound emitters comprise a multiplicity of transducers, as shown in FIG. 2.

Figure 3:
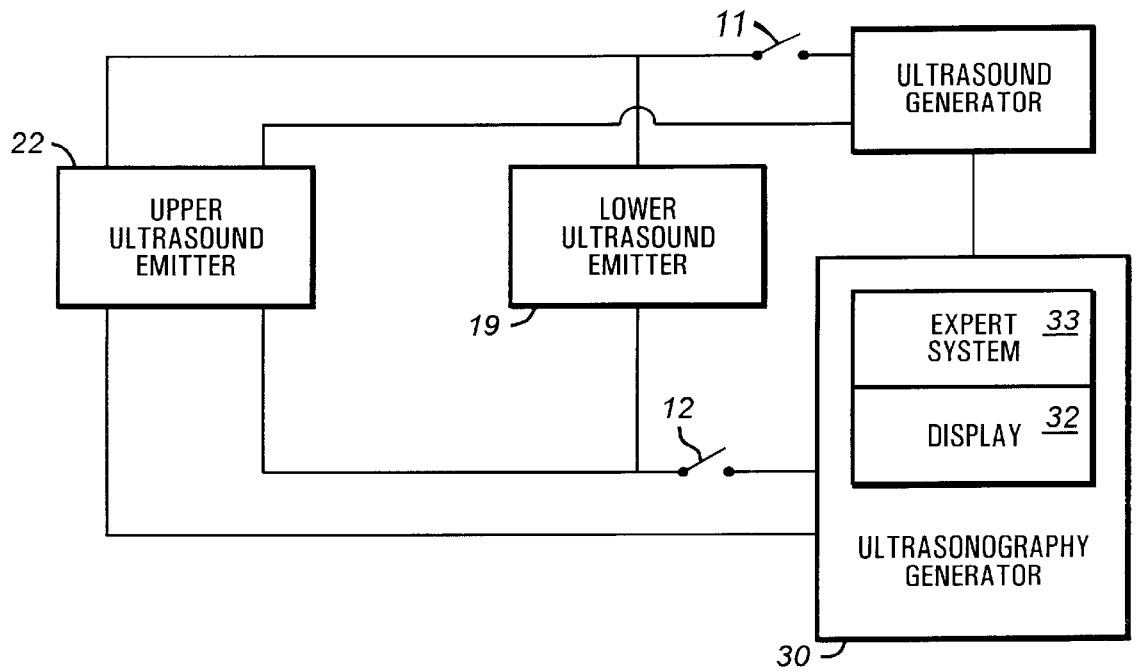
FIG. 3 is a block diagram of a second apparatus embodiment of the present invention.

In the preferred embodiment shown in FIGS. 2–3, the invention further comprises an ultrasonography generator 30 connected to at least one transducer in each transducer mounting assembly and an ultrasonography trigger 12 mounted in the portable housing and connected to the ultrasonography generator. In a preferred embodiment the ultrasonography generator and the ultrasound generator are each connected to at least two ultrasound transducers in each of the transducer mounting assemblies. In a preferred embodiment the ultrasonography generator is a doppler ultrasound unit.

The ultrasonography generator is suitable for monitoring penile hemodynamic parameters, such as blood flow. Ultrasonographic apparatus suitable for use with the present invention are disclosed in the following U.S. Pat. No. 4,612,937 to Miller; and U.S. Pat. No. 4,334,543 to Fehr. The full disclosures of these two patents are incorporated herein by reference. In a preferred embodiment, the ultrasonography generator may comprise a display 32 for displaying measured hemodynamic parameters and/or an expert system 33 capable of analyzing measured hemodynamic parameters. The expert system is capable of comparing one or measured hemodynamic parameters to preestablished parameter limits, such as maximum blood pressure or maximum blood temperature. The expert system is further capable of generating an instruction to the user to stop ultrasound therapy if predetermined parameter limits are exceeded. These instructions may be generated via the display on the ultrasonography generator or by other visual or audible means of communication.

In another embodiment, the expert system is capable of generating an open circuit signal to the ultrasound generator in the event that preestablished limits are exceeded for selected hemodynamic parameters. In this embodiment, the expert system functions as a control circuit for the ultrasound generator. In a preferred embodiment, measured hemodynamic parameter data may be transmitted to a remote location by a variety of data transmission means, including telephone lines and wireless communication.

Figure 1A:
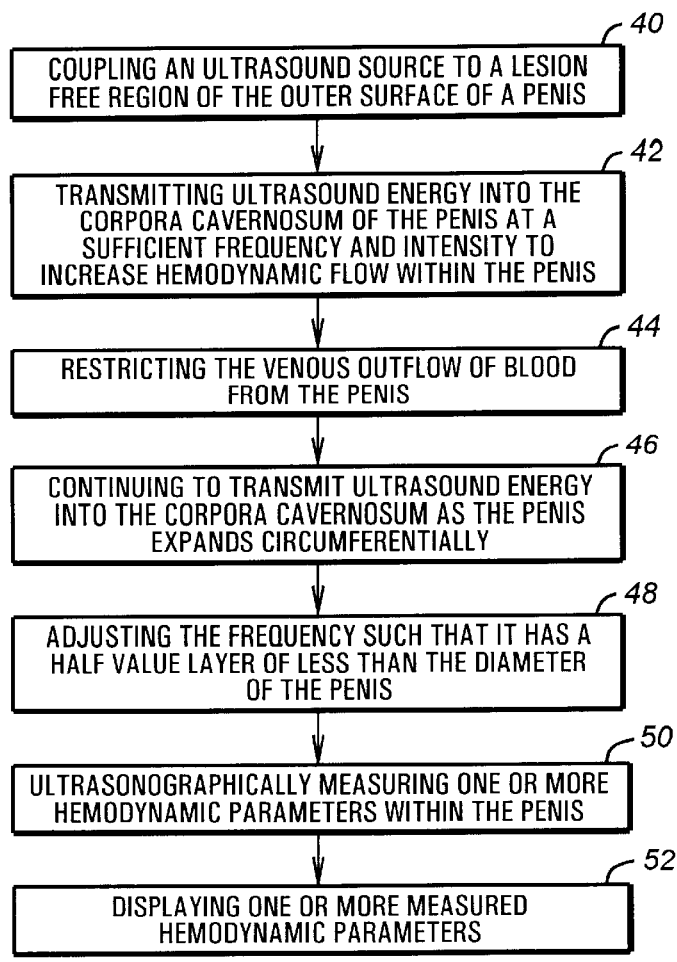
FIG. 1A is a block diagram of a first method embodiment of the present invention.
Figure 1B:
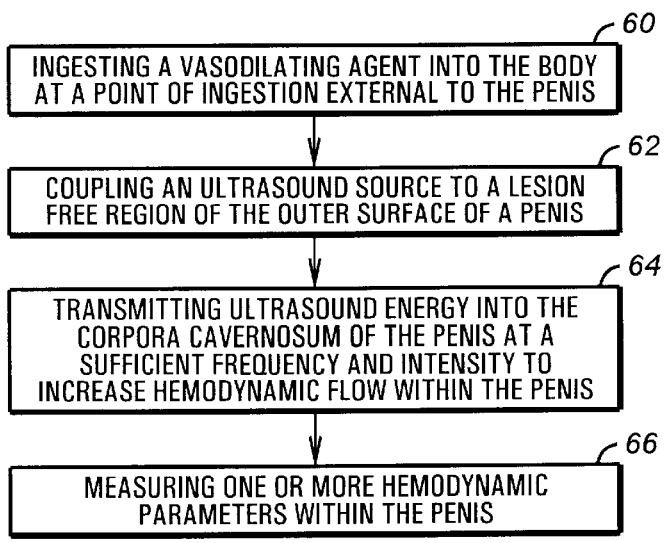
FIG. 1B is a block diagram of a second method embodiment of the present invention.

The present invention also provides a method for stimulating hemodynamic activity within a penis, as shown in FIGS. 1A–1B. The method comprises coupling an ultrasound source to the outer surface of a penis, as shown in block 40 of FIG. 1A. In a preferred embodiment the source of ultrasound energy is coupled to a lesion free region on the outer surface of the penis. In a preferred embodiment the source of ultrasound energy comprises at least two ultrasound transducers, placed on opposite sides of the penis, as shown in FIG. 2. In another preferred embodiment the source of ultrasound energy comprises a portable housing comprising the transducers.

The method further comprises transmitting ultrasound energy into the corpora cavernosum of the penis at a sufficient frequency and intensity to increase hemodynamic flow within the penis, as shown in block 42 of FIG. 1A. It is known in the ultrasound arts that 1 MHz ultrasound has a half value layer of 3.0 cm in muscle, while 3 MHz ultrasound has a half value layer of 1.0 cm in muscle. The term "half value layer", as used herein refers to the distance that ultrasound energy travels in a medium before half of the energy is absorbed. The half value layers of various ultrasound frequencies in muscle are disclosed in U. S. Pat. No. 5,413,550 to Castel. It is desirable that the frequency used be such that its half value layer will be less than the diameter of the penis being treated. In a preferred embodiment of the present invention, the frequency is adjusted such that it has a half value layer of less than the diameter of the penis being treated, as the penis expands circumferentially, as shown in blocks 46 and 48 of FIG. 1A. In a preferred embodiment, the ultrasound energy should be applied at an intensity or power density of 1.0–2.0 watts/square cm.

The transmission of ultrasound energy may be either pulsed or continuous. In a preferred embodiment the invention further comprises restricting the venous outflow of blood from the penis, as shown in block 44 of FIG. 1A.

In another preferred embodiment the invention further comprises ultrasonographically measuring one or more hemodynamic parameters within the penis, as shown in blocks 50 and 66 of FIGS. 1A and 1B, respectively. In a preferred embodiment, the ultrasonographic measuring may be performed with a doppler ultrasound unit.

In a preferred embodiment the ultrasonographic measuring comprises a measurement of blood flow velocity or blood pressure. In another preferred embodiment the transmitting and measuring steps are performed in alternating series. In a preferred embodiment, the invention further comprises displaying said measured hemodynamic parameters, as shown in block 52 of FIG. 1A.

The present invention is also directed to method for accelerating the delivery of a vasodilating agent to produce a penile erection as shown in FIG. 1B. This embodiment of the invention comprises ingesting a vasodilating agent into the body at a point of ingestion external to the penis, as shown in block 60 of FIG. 1B. In a preferred embodiment, the vasodilating agent is a PDE inhibitor or an alpha adrenergic blocker. In another preferred embodiment, the vasodilating agent is phentolamine mesylate, phentolamine hydrochloride, phenoxybenzamine yohimbine, organic nitrates, thymoxamine, imipramine, verapamil, isoxsuprine, naftidrofuryl, tolazoline, or papaverine. In a preferred embodiment the ingesting is transmucosal, transdermal, intranasal, or rectal ingesting. In another preferred embodiment, the ingesting is oral.

The invention further comprises coupling an ultrasound source to a lesion free region of the outer surface of a penis, as shown in block 62 of FIG. 1B. The invention further comprises transmitting ultrasound energy into the corpora cavernosum of the penis at a sufficient frequency and intensity to increase hemodynamic flow within the penis, as shown in block 64 of FIG. 1B.

The embodiments of the invention disclosed herein are illustrative and explanatory. Various changes in size, shape, material, as well as in the details of construction illustrated herein may be made without departing from the scope of the invention.

What is claimed is:

1. A method for accelerating the delivery of a vasodilating agent in a patient's body comprising:
   a. ingesting a vasodilating agent into the body at a point of ingestion external to the penis;
   b. coupling an ultrasound source to a lesion free region of the outer surface of the penis; and
   c. transmitting ultrasound energy through the lesion free region of the penis into the corpora cavernosum of the penis at a sufficient frequency and intensity to increase hemodynamic flow within the penis.

2. The method of claim 1, wherein said ingesting is oral.

3. The method of claim 1, wherein said ingesting is transmucosal.

4. The method of claim 1, wherein said ingesting is intranasal.

5. The method of claim 1, wherein said ingesting is rectal.

6. The method of claim 1, wherein said ingesting a vasodilating agent is accomplished by ingesting a PDE inhibitor.

7. The method of claim 1, wherein said ingesting a vasodilating agent is accomplished by ingesting an alpha adrenergic blocker.

8. The method of claim 1, wherein said ingesting a vasodilating agent is accomplished by ingesting phentolamine mesylate, phentolamine hydrochloride, phenoxybenzamine yohimbine, organic nitrates, thymoxamine, imipramine, verapamil, isoxsuprine, naftidrofuryl, tolazoline, or papaverine.

9. The method of claim 1 further comprising ultrasonographically measuring one or more hemodynamic parameters within the penis.

10. A method for stimulating hemodynamic activity within a penis, comprising:
    a. ingesting a vasodilating agent into the body as a point of ingestion external to the penis;
    b. coupling an ultrasound source comprising at least two transducers, to a lesion free region of the outer surface of the penis; and
    c. transmitting ultrasound energy through the lesion free region of the penis into the corpora cavernosum of the penis at a sufficient frequency and intensity to increase hemodynamic flow within the penis.

11. The method of claim 10, wherein said coupling comprises coupling at least two ultrasound transducers to opposite sides of the penis.

12. The method of claim 10, wherein said transmitting occurs at a power density in the range of 1.0–2.0 watts per square centimeter.

13. The method of claim 10, wherein said transmitting occurs at a frequency in the range of 1.8–3.5 MHz.

14. The method of claim 10, wherein said transmitting comprises moving the ultrasound source relative to the penis so as to disperse the transfer of thermal energy.

15. The method of claim 10, wherein said ingesting is oral.

16. The method of claim 10, wherein said ingesting is selected from the group consisting of transmucosal, intranasal, and rectal.

17. A method for stimulating hemodynamic activity within a penis, comprising:
    a. ingesting a vasodilating agent into the body as a point of ingestion external to the penis;
    b. coupling an ultrasound source comprising at least two transducers mounted in a curved housing, to the lesion free region of the outer surface of a penis; and
    c. transmitting ultrasound energy through the lesion free region of the penis into the corpora cavernosum of the penis at a sufficient frequency and intensity to increase hemodynamic flow within the penis.

18. The method of claim 17, wherein said transmitting occurs at a frequency in the range of 1.8–3.5 MHz.

19. The method of claim 17, wherein said ingesting is oral.

* * * * *